United States Patent [19]

Lies

[11] 4,025,532
[45] May 24, 1977

[54] 2-(O-TOLYL)IMINO-1,3-DITHIOLES, A METHOD FOR PREPARING THE SAME, AND THEIR UTILIZATION AS IXODICIDES

[75] Inventor: Thomas Andrew Lies, Princeton, N.J.

[73] Assignee: American Cyanamid Company, Stamford, Conn.

[22] Filed: Feb. 17, 1976

[21] Appl. No.: 658,154

Related U.S. Application Data

[63] Continuation of Ser. No. 519,460, Oct. 31, 1974, abandoned.

[52] U.S. Cl. .......................... 260/327 M; 424/277
[51] Int. Cl.² ...................................... C07D 339/06
[58] Field of Search ............................... 260/327 M

[56] References Cited
UNITED STATES PATENTS

| | | | |
|---|---|---|---|
| 3,389,147 | 6/1968 | Addor | 260/327 |
| 3,433,803 | 3/1969 | Ottmann et al. | 260/327 |
| 3,564,013 | 2/1971 | Walsh | 260/327 |
| 3,842,096 | 10/1974 | Brand et al. | 260/327 |

Primary Examiner—Cecilia M. S. Jaisle
Attorney, Agent, or Firm—Harry H. Kline

[57] ABSTRACT

There is provided an ixodicidal and chemosterilant compound having the formula:

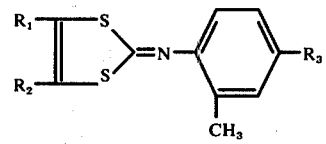

where $R_1$ and $R_2$ may be the same or different and are hydrogen, straight chain or branched alkyl ($C_1$–$C_4$), and $R_3$ is hydrogen, halogen or alkyl ($C_1$–$C_3$), and a method for preparing the same, as well as ixodicidal and chemosterilant compositions containing said compound or mixtures thereof.

3 Claims, No Drawings

2-(O-TOLYL)IMINO-1,3-DITHIOLES, A METHOD FOR PREPARING THE SAME, AND THEIR UTILIZATION AS IXODICIDES

This application is a continuation of my copending application, Ser. No. 519,460, filed on Oct. 31, 1974, now abandoned The present invention relates to novel compounds having ixodicidal and chemosterilant utility. More particularly, it relates to 2-(o-tolyl)imino-1,3-dithioles represented by the formula:

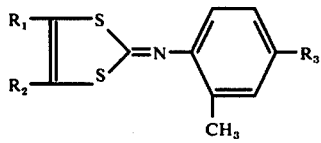

where $R_1$ and $R_2$ are the same or different and are hydrogen, or straight chain or branched alkyl ($C_1'-c_4$), and $R_3$ is hydrogen, halogen or alkyl ($C_1-C_4$) and to a method for preparing the same by the acid catalyzed ring closure of certain dithiocarbamate esters hereinbelow defined. Still more particularly, the invention is concerned with the use of the aforedefined derivatives of 2-(o-tolyl)imino-1,3-dithiole in the control of ixodid ticks.

Illustrative of the compounds of the invention are:
2-(4-chloro-o-tolyl)imino-4-methyl-1,3-dithiole,
2-(4-chloro-o-tolyl)imino-1,3-dithiole,
2-(o-tolyl)imino-4-methyl-1,3-dithiole,
2-(2,4-dimethylphenyl)imino-4-methyl-1,3-dithiole,
2-(4-bromo-o-tolyl)imino-4-ethyl-1,3-dithiole, and
2-(4-iodo-o-tolyl)imino-4-propyl-1,3-dithiole.

The novel compounds of the present invention can be prepared in a straightforward manner by an acid-catalyzed cyclization of a 2-chloroallyl ester of substituted dithiocarbanilic acid at a temperature ranging from about 50° C. to about 120° C. The reaction can be graphically represented as follows:

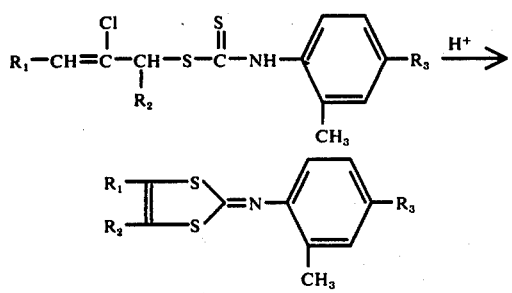

wherein $R_1$, $R_2$ and $R_3$ are defined as above. As the non-oxidizing acid, hydrochloric acid is preferably employed, although any equivalent thereof may be substituted therefor. If desired, the above reaction can be carried out in an inert solvent, such as water, methanol, ethanol, isopropanol, acetone, methylethylketone, or mixtures thereof.

An alternative procedure, which may be employed to prepare the novel compounds herein, comprises the steps of reacting the disodium salt of ethylene-1,2-dithiol with a substituted phenylisocyanide dichloride in an inert solvent medium at relatively low temperatures ranging from 0° C. to 50° C. The reaction can graphically be represented as follows:

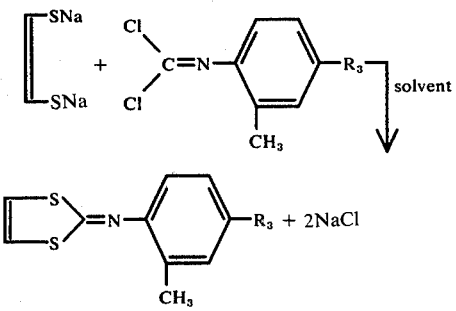

where $R_3$ is hydrogen, halogen or alkyl ($C_1-C_3$).

Advantageously, the hereinabove defined 2-(o-tolyl)imino-1,3-dithioles can be employed to control infestations of ixodid ticks on mammals and birds, and particularly to control tick infestations of domestic and farm animals such as cattle, swine, sheep and goats, domestic pets, such as dogs, cats, rabbits, poultry such as chickens, turkeys or geese, and fur bearing animals, such as mink, foxes or chinchillas. In general, the compounds of the invention are used to control ixodid ticks when they are applied to and brought in contact with said ticks in effective ixodicidal amounts. Alternatively, the habitat or the host animal of said ticks can be treated with sprays, dusts, dips or drenches containing effective, ixodicidal amounts of the compounds of this invention. The term "effective ixodicidal amount" is used to define the amount of an active compound of the invention present in a dilute formulation in the range of 1 to 5000 ppm and, preferably, in the range of 200 to 2000 ppm, wherein said dilute formulations are utilized as described hereinbelow.

It is a good practice that the active compounds herein be formulated with known solid or liquid diluents or other known formulation aids. They may be formulated as dusts, dust concentrates, wettable powders, emulsifiable concentrates and the like. For instance, dusts and dust concentrates can be prepared by blending the active 1,3-dithiole compound with inert diluents such as attapulgite, kaolin, or walnut shell flour. Dusts usually contain from about 1 to about 15% by weight of acitve ingredient, while dust concentrates may contain 16 to about 85% by weight of active ingredient. Wettable powders may similarly be formulated except that such formulations can contain wetting agents, such as alkylbenzeneethyleneoxide condensates, alkylnaphthalene sulfonates, or sodium N-methyl-N-oleoyl taurate, usually in amounts ranging from about 0.1% to about 2% to achieve dispersion of the powder in water.

The compounds of the present invention can also be formulated as emulsifiable concentrates by dissolving or dispersing about 10% to 75% by weight of the active ingredient in a solvent such as water, an alcohol ($C_1-C_3$), chlorobenzene, xylene or cyclohexanone, in the presence of suitable emulsifiers and dispersing agents.

Emulsifiable concentrates and wettable powders are eminently useful, since they can be diluted with water or other suitable solvents adjusted to the proper concentration and applied as dilute sprays to an infested area or to an infested animal, or may be applied topically to an animal for which protection is sought. These dilute solutions may be employed equally well as dips.

As ixodicidal and chemosterilant agents, generally about 1 ppm to 5000 ppm and, preferably, 200 ppm to 2000 ppm of the substituted 2(0-tolyl)imino-1,3-dithioles is effective for preventing the embryogenesis of trick ova.

To facilitate a further understanding of the invention, the following examples are presented primarily for the purpose of illustrating certain more specific details thereof. The invention is not to be deemed limited except as defined in the claims. Unless otherwise noted, all parts are by weight.

EXAMPLE 1

Preparation of
2-(4-chloro-o-tolyl)imino-4-methyl-1,3-dithiole

2-Chloroallyl 4-chloro-2-methyldithiocarbanilate (12.0 g, 0.041 mol), concentrated hydrochloric acid (14.0 ml, ca 0.16 mol) and ethanol (6.0 ml) are mixed in a suitable reaction vessel and heated at reflux for 2 hours. Ethanol (4.0 ml) is then added and the reaction mixture is refluxed an additional five hours. The resulting clear brown solution is evaporated to dryness in vacuo (50° C. maximum temperature). A gummy solid residue, 2-(4-chloro-o-tolyl)imino-4-methyl-1,3-dithiole hydrochloride, is dissolved in acetone and reprecipitated from the solution with ether. The precipitate is filtered off, washed with ether, and dried at room temperature. The product weighs 9.6 g, corresponding to an 80% yield. It is further purified by precipitation from an acetone/ether mixture at below 0° C. The product is isolated, washed with ether and dried at room temperature. The product weighs 8.9 g and has a melting point of 161° – 183° C.

The product is then dissolved in water and the solution is made slightly alkaline to a pH 7.7 to 8.0 with sodium bicarbonate. The latter is then extracted with ether. The ether solution is washed with water and is then dried over anhydrous magnesium sulfate. The ethereal solution is evaporated to dryness in vacuo with gentle heating leaving a viscous amber oil (7.2 g) containing the desired 2-(4-chloro-o-tolyl)imino-4-methyl-1,3-dithiole. The oil is purified by chromatographing a chloroform solution of it on a dry, activated silica gel colmun and is recovered from the solution by removing the chloroform in vacuo. About 6.7 g of the product, a yellow, slightly turbid viscous oil is obtained.

Analysis: Calculated for $C_{11}H_{10}ClNS_2$: C, 51.65; H, 3.94; N, 5.48. Found: C, 51.74; H, 4.01; N, 5.51.

EXAMPLE 2

The reactant, 2-chloroallyl 4-chloro-2-methyldithiocarbanilate employed in Example 1 above, is prepared as follows:

To a stirred solution of 2,3-dichloropropene (29.2 g, 0.26 mol) in methanol (200 ml) triethylammonium 4-chloro-2-methyldithiocarbanilate (63.8 g, 0.2 mol) is added in small portions over 30 minutes at 27°-30°0 C. The reaction mixture is stirred two hours and is then poured on cracked ice. The crude 2-chloroallyl 4-chloro-2-methyldithiocarbanilate separates as an oil weighing 50.5 g. The crude product is mixed with carbon tetrachloride (250 ml) and filtered cold to remove precipitated solids. The carbon tetrachloride is removed from the clarified solution by evaporation leaving an oil which begins to crystallize.

A mixture of hexane and pentane is added to the residue and the resulting yellow solid is filtered off and washed with pentane. It is then redissolved in chloroform and chromatographed on a dry, activated silica gel column. The part of the column containing the 2-chloroallyl 4-chloro2-methyldithiocarbanilate is separated and is eluted with ethyl acetate. On standing, the ethyl acetate solution deposits a crystalline solid. The crystalline solid is isolated by decantation, washed with hexane and dried to yield crystalline 2-chloroallyl 4-chloro-2-methyldithiocarbanilate, which is further purified by recrystallization from a mixture of chloroform and hexane. The 2-chloroallyl 4-chloro-2-methyldithiocarbanilate is isolated, washed with hexane and dried. The resulting purified 2-chloroallyl 4-chloro-2-methyldithiocarbanilate has a melting point of 88° –90.5° C.

EXAMPLE 3

The reactant, 2-chloro-1-methyl-2-butenyl 4-chloro2-methyldithio-carbanilate is prepared by following the procedure of Example 2 wherein 3,4-dichloro-2-pentene and triethylammonium 4-chloro-2-methyldithiocarbanilate are reacted.

EXAMPLE 4

The procedure of Example 1 is repeated in every detail except that 2-chloro-1-methyl-2-butenyl 4-chloro-2-methyldithio carbanilate as prepared in Example 3 is employed as the reactant to form 2-(4-chloro-o-tolyl)imino-4-ethyl-5-methyl-1,3-dithiole.

EXAMPLE 5

By the procedure of Example 2, the reactant 2-chloro-1-isopropylallyl 4-chloro-2-methyl dithiocarbanilate is prepared by the reaction of 2,3-dichloro-4-methyl-1-pentene and triethylammonium 4-chloro-2-methyldithiocarbanilate. The 2,3-dichloro-4-methyl-1-pentene is prepared by the reaction of isobutyraldehyde with acetylenemagnesium bromide to yield 4-methyl-1-pentyn-3-ol, which is converted to 2-chloro-4-methyl-1-pentene-3-ol by treatment with hydrogen chloride in the presence of mercuric chloride. The required 2,3-dichloro-4-methyl-1-pentene is then obtained by treating 2-chloro-4-methyl-1-pentene-3-ol with phosphorus trichloride.

EXAMPLE 6

By the procedure of Example 1, 2-chloro-1-isopropylallyl 4-chloro-2-methyldithiocarbanilate prepared in Example 5 is cyclized to yield 2-(4-chloro-o-tolyl)imino-4-isopropyl-5-methyl-1,3-dithiole.

EXAMPLE 7

By the procedure of Example 1, 2-chloroallyl 4-bromo-2-methyldithiocarbanilate is prepared substituting triethylammonium 4-bromo-2-methyldithiocarbanilate for the 4-chloro derivative of the same and cyclized as in Example 1 to yield 2-(4-bromo-o-tolyl)imino-4-methyl-1,3-dithiole in good yield and purity.

EXAMPLE 8

By the procedure of Example 1, the 2-chloro-2-butenyl 4-bromo-2-methyldithiocarbanilate is cyclized to 2-(4-bromo-o-tolyl)imino-4-ethyl-1,3-dithiole.

EXAMPLE 9

By the procedure of Example 1, the 2-chloro-2-pentene-1-yl ester of 4-iodo-2-methyldithiocarbanilic acid is cyclized to 2(4-iodo-o-tolyl)imino-4-propyl-1,3-dithiole.

EXAMPLE 10

Preparation of 2-(4-chloro-o-tolyl)imino-1,3-dithiole

In a suitable reaction vessel, disodium ethylene 1,2-dithiol (4.1 g, 0.03 mol) and acetone (100 ml) are mixed and 4-chloro-o-tolylisocyanide dichloride (6.25 g, 0.028 mol) is added dropwise with cooling under a nitrogen atmosphere, starting at room temperature. After the addition, the temperature rises to 29° C. The reaction mixture is stirred for about 16 hours and is then concentrated in vacuo. The residue is dissolved in ether and water. The ether layer is then washed with 12 ml of 6N hydrochloric acid. The small amount of solid precipitated from the ether-acid mixture is isolated and is combined with the aqueous acidic layer. The aqueous acidic layer is then neutralized with sodium hydroxide and the product is taken up in ether. The ether solution is dried over anhydrous magnesium sulfate and is concentrated in vacuo. A beige-colored solid weighing 2.4 g and having a melting point of 72°–74° C. is obtained. The recovered product corresponds to a 35% yield.

Analysis: Calculated for $C_{10}H_8ClNS_2$: C, 49.69; H, 3.31; N, 5.80. Found: C, 49.70; H, 3.31; N, 5.79.

EXAMPLE 11

The procedure of Example 4 is followed in every detail except that 4-bromo-o-tolylisocyanide dichloride is substituted for the corresponding 4-chloro derivative of Example 4. 2-(4-Bromo-o-tolyl)imino-1,3-dithiole is obtained in good yield and purity.

EXAMPLE 12

Preparation of 2-phenylimino-4-methyl-1,3-dithiole

In a suitable reaction vessel, 2-chloroallyl dithiocarbanilate (20.3 g, 0.0834 mol) and concentrated hydrochloric acid (26.2 ml, ca. 0.326 mol) are mixed and heated at reflux temperatures for 5 hours. The resulting solution is cooled to room temperature and is diluted with water. Solid sodium carbonate is added to the solution to raise the pH to 6 and the reaction mixture is then extracted with ether. The ether layer is separated and washed with 6N hydrochloric acid. The resulting aqueous acidic layer is neutralized with sodium carbonate and the separated product is extracted with ether. The ether layer is washed with water, dried over anhydrous magnesium sulfate and evaporated to dryness in vacuo to leave crude 2-phenylimino-4-methyl-1,3-dithiole which crystallizes on standing. The crude product is recrystallized from petroleum ether to yield 8.8 g of the purified product, a tan solid melting at from 44.5° C. to 49.5° C.

Analysis: Calculated for $C_{10}H_9NS_2$: C, 57.93; H, 4.38; N, 6.76. Found: C, 57.88; H, 4.38; N, 6.70.

EXAMPLE 13

Preparation of 2(p-tolyl)imino-4-methyl-1,3-dithiole

2-Chloroallyl 4-methyldithiocarbanilate (7.3 g, 0.0286 mol) and concentrated hydrochloric acid (9.1 ml 0.112 mol) are mixed and heated at reflux temperature for 2 hours. The resulting solution is cooled, diluted with water, and neutralized with sodium carbonate. The reaction mixture is extracted with ether. The ether extract is washed with 6N hydrochloric acid and the aqueous layer is separated, neutralized with sodium carbonate, and extracted with ether. The ether phase is separated, washed with water and dried over anhydrous magnesium sulfate. The ether is evaporated to dryness in vacuo to leave 5.0 g of crude 2-(p-tolyl)imino-4-methyl-1,3-dithiole, a brown oil which crystallizes on standing. The crystalline mass is triturated with petroleum ether, filtered off and dried to yield 2.7 g of purified product melting at from 46.5° C. to 49.5° C.

Analysis: Calculated for $C_{11}H_{11}NS_2$: C, 59.69; H, 5.01; N, 6.33. Found: C, 59.77; H, 5.02; N, 6.38.

EXAMPLE 14

Preparation of 2-(o-tolyl)imino-4-methyl-1,3-dithiole

The procedure of Example 6 is employed in every detail to cyclize 2-chloroallyl 2-methyldithiocarbanilate (23.8 g, 0.0924 mol) to obtain 17.6 g of the product, melting at 65.5° C. to 69° C.

Analysis: Calculated for $C_{11}H_{11}NS_2$: C, 59.69; H, 5.01; N, 6.33. Found: C, 59.61; H, 5.01; N, 6.35.

EXAMPLE 15

Preparation of 2-(o,p-2,4-dimethylphenyl)imino-4-methyl-1,3-dithiole

The procedure of Example 6 is repeated to cyclize 2-chloroally 2,4-dimethyldithiocarbanilate (23.8 g, 0.087 mol) to obtain 18.8 g. of the product, a yellow oil.

Analysis: Calculated for $C_{12}H_{13}NS_2$: C, 61.23; H, 5.57; N, 5.95. Found: C, 61.37; H, 5.57; N, 5.95.

EXAMPLE 16

Chemosterilization of ixodidae and suppression of fecundity of ixodidae

The efficacy of the compounds of the present invention for suppression of tick fecundity is illustrated in the following tests wherein engorged adult female Boophilus microplus ticks which have dropped from cattle are collected and used for testing.

The compound to be tested is dissolved in a 35/65 acetone/water mixture in sufficient amount to provide 500 ppm., 1,000 ppm. and 2,000 ppm. of compound in the test solutions. Ten ticks per treatment are used. They are then immersed in the test solution for three to five minutes, removed, and placed in dishes and held in incubators for 2 to 3 weeks at 28° C. Counts of ticks laying eggs are then made and recorded. Eggs which were laid are placed in containers and kept for one month to observe hatching and to determine chemosterilant effect. For each test, ten non-resistant (S) ticks as well as ten ethion-resistant (M) and ten dioxathion resistant (D) ticks are used, since the latter two are among the most difficult of their kind to control. Results of these tests are presented in Tables I and II below. It will be noted that Table I displays under the column headings: P (partial oviposition), T (total oviposition) and S (sterile) the number of ticks laying eggs (P and T,) and the number of ticks sterile (S, i.e. no hatch). Table II displays the summation of scores found in Table I. The rating system used for each tick in Table I is as follows:

| Rating System | |
|---|---|
| Result | Score |
| No oviposition | 4 |
| Partial oviposition, no hatch | 3 |
| Total oviposition, no hatch | 2 |
| Partial oviposition, viable eggs | 1 |

-continued

| Result | Rating System | Score |
|---|---|---|
| Normal oviposition and hatch | | 0 |

The rating system is based on the summation of scores from all ticks regardless of the dose rate or strain of ticks tested. Using this rating system the best score possible would be 360, or 90 (the total number of ticks used) × 4 (the highest score). The efficacy is reported as percent of the best possible score.

TABLE I

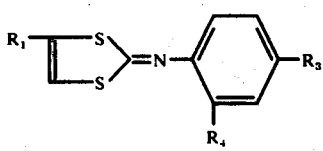

| Structure | | | Rate | Strain | | | | | | | | | | | |
|---|---|---|---|---|---|---|---|---|---|---|---|---|---|---|---|
| | | | | M | | | | D | | | | S | | | |
| $R_1$ | $R_3$ | $R_4$ | ppm | P | S | T | S | P | S | T | S | P | S | T | S |
| H | Cl— | $CH_3$ | 2,000 | 0 | | 0 | | 2 | 1 | 0 | | 1 | | 0 | |
| | | | 1,000 | 3 | | 2 | | 1 | 1 | 0 | | 1 | | 0 | |
| | | | 500 | 1 | | 8 | | 4 | 1 | 0 | | 1 | | 0 | |
| $CH_3$ | Cl— | $CH_3$ | 2,000 | 1 | 1 | 0 | | 0 | | 0 | | 0 | | 0 | |
| | | | 1,000 | 5 | 2 | 1 | | 0 | | 0 | | 0 | | 0 | |
| | | | 500 | 4 | 3 | 3 | | 2 | 2 | 0 | | 0 | | 0 | |
| $CH_3$ | H— | $CH_3$ | 2,000 | 6 | 2 | 0 | | 2 | 1 | 0 | | 3 | | 0 | |
| | | | 1,000 | 3 | | 3 | | 2 | | 0 | | 3 | | 0 | |
| | | | 500 | 1 | | 5 | | 5 | | 0 | | 4 | | 4 | |
| $CH_3$ | $CH_3$ | $CH_3$ | 2,000 | 1 | 1 | 7 | | 0 | | 7 | | 1 | 1 | 0 | |
| | | | 1,000 | 1 | 1 | 7 | | 1 | 1 | 6 | | 1 | 1 | 1 | |
| | | | 500 | 0 | | 9 | | 1 | 1 | 9 | | 3 | | 1 | |
| $CH_3$ | H | H | 2,000 | 0 | | 8 | | 0 | | 9 | | 0 | | 9 | |
| | | | 1,000 | 0 | | 8 | | 0 | | 9 | | 0 | | 10 | |
| | | | 500 | 1 | 1 | 7 | | 0 | | 9 | | 0 | | 9 | |
| $CH_3$ | $CH_3$ | H | 2,000 | 2 | | 6 | | 2 | 2 | 7 | | 1 | | 6 | |
| | | | 1,000 | 2 | 1 | 7 | | 3 | | 7 | | 1 | | 9 | |
| | | | 500 | 0 | | 1 | 1 | 1 | | 9 | | 0 | | 10 | |
| $CH_3$ | $CF_3$ | H | 2,000 | 0 | | 10 | | 0 | | 8 | | 0 | | 9 | |
| | | | 1,000 | 0 | | 10 | | 1 | | 5 | | 0 | | 9 | |
| | | | 500 | 0 | | 8 | | 0 | | 7 | | 0 | | 10 | |

TABLE II

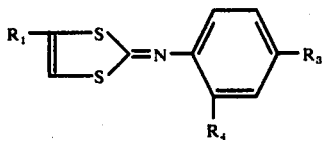

| Structure | | | Efficacy % |
|---|---|---|---|
| $R_1$ | $R_3$ | $R_4$ | |
| H— | Cl— | $CH_3$ | 80 |
| $CH_3$ | Cl— | $CH_3$ | 90 |
| $CH_3$ | H— | $CH_3$ | 64 |
| $CH_3$ | $CH_3$ | $CH_3$ | 44 |

TABLE II-continued

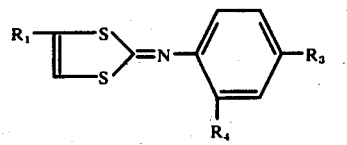

| Structure | | | Efficacy % |
|---|---|---|---|
| $R_1$ | $R_3$ | $R_4$ | |
| $CH_3$ | H— | H— | 13 |
| $CH_3$ | $CH_3$ | H— | 13 |
| $CH_3$ | $CF_3$ | H— | 15 |

It is clear from the above tables that the compounds of the present invention exhibit marked enhancement as ixodicides as contrasted to the utilization of compounds in which the phenyl substituent is unsubstituted.

I claim:

1. A compound of the formula:

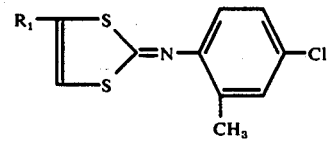

wherein $R_1$ is a member selected from a group consisting of hydrogen and methyl.

2. The compound according to claim 1 wherein $R_1$ is hydrogen.

3. The compound according to claim 1 wherein $R_1$ is methyl.

* * * * *